(12) United States Patent
Buurlage

(10) Patent No.: US 9,597,167 B2
(45) Date of Patent: Mar. 21, 2017

(54) IMPLANT

(71) Applicant: LAKEVIEW INNOVATION LTD., Buochs (CH)

(72) Inventor: Thorsten Buurlage, Gorxheimertal (DE)

(73) Assignee: LAKEVIEW INNOVATION LTD., Buochs (CH)

( * ) Notice: Subject to any disclaimer, the term of this patent is extended or adjusted under 35 U.S.C. 154(b) by 0 days.

(21) Appl. No.: 13/916,175

(22) Filed: Jun. 12, 2013

(65) Prior Publication Data

US 2013/0337409 A1 Dec. 19, 2013

(30) Foreign Application Priority Data

Jun. 13, 2012 (EP) ..................... 12004462

(51) Int. Cl.
*A61C 8/00* (2006.01)
*A61K 6/02* (2006.01)

(52) U.S. Cl.
CPC .......... *A61C 8/0025* (2013.01); *A61C 8/0018* (2013.01); *A61C 8/0022* (2013.01); *A61C 8/0037* (2013.01); *A61K 6/024* (2013.01); *A61C 8/0012* (2013.01)

(58) Field of Classification Search
CPC ..... A61C 8/0018; A61C 8/0022; A61C 8/005; A61C 8/0025; A61C 8/0037; A61C 8/0012; A61B 17/8057; A61B 17/863; F16B 35/0068; F16B 35/048; A61K 6/024
USPC ............. 433/172–176, 201.1; 411/424
See application file for complete search history.

(56) References Cited

U.S. PATENT DOCUMENTS

| | | | | |
|---|---|---|---|---|
| 4,653,244 | A * | 3/1987 | Farrell | 52/745.21 |
| 4,723,913 | A * | 2/1988 | Bergman | 433/173 |
| 4,780,081 | A * | 10/1988 | Enomoto et al. | 433/174 |
| 5,094,618 | A * | 3/1992 | Sullivan | 433/173 |
| 5,108,289 | A * | 4/1992 | Fukuyo | 433/173 |
| 5,310,343 | A * | 5/1994 | Hasegawa et al. | 433/173 |
| 5,360,448 | A * | 11/1994 | Thramann | 606/60 |
| 5,375,956 | A * | 12/1994 | Pennig | 411/389 |
| D358,212 | S * | 5/1995 | Sullivan | D24/156 |
| D366,115 | S * | 1/1996 | Sullivan | D24/156 |
| 5,591,029 | A * | 1/1997 | Zuest | 433/173 |
| 5,607,428 | A * | 3/1997 | Lin | 606/287 |

(Continued)

FOREIGN PATENT DOCUMENTS

| | | |
|---|---|---|
| DE | 197 18 175 A1 | 11/1998 |
| EP | 2 283 793 A1 | 2/2011 |
| WO | WO 2007/090529 A1 | 8/2007 |

OTHER PUBLICATIONS

European Search Report dated Nov. 15, 2012.
Aug. 17, 2016 Chinese Office Action issued by SIPO in Chinese Application No. 201310234024.9.

*Primary Examiner* — Chris L Rodriguez
*Assistant Examiner* — Hao D Mai
(74) *Attorney, Agent, or Firm* — Buchanan Ingersoll & Rooney PC

(57) ABSTRACT

The present disclosure relates to an implant, such as a dental implant, having a base member and a thread arranged at an outer end of the base member. The dental implant can be easily inserted and good footing of the implant in the bone can be achieved. Annular ridges and/or recesses can be formed in a section of the base member having no thread.

17 Claims, 3 Drawing Sheets

(56) References Cited

U.S. PATENT DOCUMENTS

| | | | |
|---|---|---|---|
| 5,755,809 A * | 5/1998 | Cohen et al. | 623/23.35 |
| 5,759,035 A * | 6/1998 | Ricci | 433/174 |
| 5,915,967 A | 6/1999 | Clokie | |
| 5,954,722 A * | 9/1999 | Bono | 606/281 |
| 6,000,892 A * | 12/1999 | Takasaki | 411/413 |
| 6,001,101 A * | 12/1999 | Augagneur et al. | 606/316 |
| 6,099,312 A * | 8/2000 | Alvaro | 433/174 |
| 6,273,720 B1 * | 8/2001 | Spalten | 433/173 |
| 6,302,913 B1 * | 10/2001 | Ripamonti et al. | 623/16.11 |
| 6,379,153 B1 * | 4/2002 | Schroering | 433/173 |
| 6,616,391 B1 * | 9/2003 | Druschel | 411/387.2 |
| 6,739,815 B2 * | 5/2004 | Takasaki | 411/387.1 |
| 6,941,635 B2 * | 9/2005 | Craven | 29/525.11 |
| 7,179,260 B2 * | 2/2007 | Gerlach et al. | 606/291 |
| 7,291,013 B2 * | 11/2007 | Aravena et al. | 433/173 |
| 7,293,947 B2 * | 11/2007 | Craven | 411/387.2 |
| 7,677,854 B2 * | 3/2010 | Langewiesche | 411/387.2 |
| 7,955,364 B2 * | 6/2011 | Ziolo et al. | 606/308 |
| 8,403,969 B2 * | 3/2013 | Wallenstein et al. | 606/289 |
| 8,728,129 B2 * | 5/2014 | Fritzinger et al. | 606/290 |
| 8,777,969 B2 * | 7/2014 | Kayan | 606/151 |
| 2003/0235483 A1 * | 12/2003 | Chen | 411/387.7 |
| 2005/0147943 A1 | 7/2005 | Chang | |
| 2006/0276793 A1 * | 12/2006 | Berry | 606/69 |
| 2007/0298379 A1 * | 12/2007 | D'Alise | 433/174 |
| 2010/0036502 A1 | 2/2010 | Syrluga et al. | |
| 2011/0039233 A1 | 2/2011 | Rebaudi | |
| 2011/0070557 A1 | 3/2011 | Elyav | |
| 2014/0030674 A1 * | 1/2014 | Nguyen | 433/173 |

\* cited by examiner

IMPLANT

The present invention relates to an implant, in particular to a dental implant, having a base member and a thread arranged at an outer end of the base member, where in the region of the base member having no thread, annular ridges and/or recesses are formed.

The use of implants for repairing damage to bones, joints or teeth has long been known. For example, implantable screws or implantable connectors are used to stabilize broken bones or for artificial joints. Even with total loss of one or more teeth, it is now common practice to recommend a dental implant. In this, a base member of the implant is anchored in the jaw, the superstructure, for example a bridge or a crown, can then be fitted onto the base member using different aids.

For example WO 2007/090529 A1 describes a implant intended to grow into a bone. The implant comprises an implant member, an implant post and a superstructure. In order to properly anchor the implant member in the jaw bone, the implant member is provided with a thread which extends across the entire length of the implant member. After the implant member has grown into the jaw bone, the implant post is attached to the implant member, the superstructure is fitted onto the implant post.

A disadvantage of this implant is that the implant is attached in the bone with the screw thread extending the full length of the implant member. For this purpose, boring a hole and cutting a thread in the bone is required. Precise insertion is therefore difficult. In particular, screwing-in is in practice tedious and challenging when space is limited.

Implants are also known that are fixed in the jaw using a press fit. Such a press fit, however, is not particularly advantageous due to the pressure on the bone and the lack of precision.

DE 197 18 175 A1 shows a further dental implant comprising a base member implantable in the jaw bone. This implant is based on the object of providing stable anchorage of the base member with small damage to the bone tissue of the patient. For this purpose, it is provided that the base member at its inner end, i.e. the end first inserted in the jaw bone, comprises a first section, to which a second section connects in which the outer diameter increases in the direction towards the outer end of the implant base member. This second section is followed by a third section which is provided with a self-tapping external thread. The outer diameter of the first section is smaller than the outer diameter of the second and third sections. This implant is also provided with a relatively long threaded section. The stability of the implant is reduced by the threads and the notch effect. Here as well, screwing-in is tedious and challenging.

A dental implant is already known from U.S. Pat. No. 5,915,967 comprising a thread at one end and is provided with annular ridges and grooves in the region on which no thread is formed. Similar implants are known from EP 2 283 793 A1, US 2010/036502 A1, US 2005/147943 A1 and US 2011/070 557 A2.

It is therefore the object of the present invention to provide an implant, which avoids the disadvantages known from prior art implants, and in particular, enables quick and accurate insertion of the implant with low pressure to the bone. Furthermore, the implant is to be designed such that the risk of loosening and thereby the loss of the implant inserted in the bone is minimized.

For this purpose, the invention proposes that the length of the region of the base member, on which the thread is disposed, correspond to about one tenth of the total length of the base member, that the thread be formed with multiple entries and that the length of the individual threads be less than the perimeter of the base member and preferably is about one quarter of the perimeter of the base member.

Due to the short thread, tapping and screwing-in the thread into the bore across the entire length of the implant is avoided. As described above, in particularly the screw-in process is tedious an difficult when space is limited. With the implant according to the invention, the base member is only inserted into an opening or bore in the bone and locked by a short twist. This is particularly simple if the thread is designed as a tapping or grove thread. This reduces the number of work steps, the implant can be inserted very precisely into the bore hole. The implant is more stable due to the lacking thread turns and therefore also the lacking notch effect. It is prevented due to the annular ridges and/or recesses that the implant comes loose and can crew itself out of the bore from the bone. The annular ridges and recesses do not need to extend completely around the perimeter of the implant, but can also have interruptions. It is important that the pitch of the annular line, on which the ridges or recesses are arranged, for one complete turn of the base member equals to zero. The annular ridges and recesses are therefore not spiral-shaped or helical, respectively, so that undesired unscrewing of the implant from the opening in the bone is prevented. It has been found that this length is sufficient for the threaded section in order to fix the implant after insertion into the bone. The pressure on the bone is kept very low. A short twist-tightening is sufficient to place and affix the implant as desired. This enables good footing of the implant in the bone despite the short length of the thread. The implant is then locked in the bone by a short turn, preferably, by one half or one quarter of the perimeter of the base member.

According to a preferred embodiment of the invention, it can be provided that the annular ridges and/or recesses are closed. This further reduces the probability of the implant moving out of the bone.

It can also be provided that the section of the base member having no thread is formed as a sliding seat. The term sliding seat is presently to be understood in that the base member in the threadless section comprises no elements projecting beyond the surface of the base member. The ridges therefore have the same maximum height as the remaining surface of the base member. This enables easy insertion of the implant in the portion of the sliding seat, the implant is simply inserted into the bore in the bone. There is no pressure to the bone as would be the case, for example, with a press fit. For fixing the implant in the bone, it is sufficient to insert the implant into the bore and then to give it a short turn in the bore, so that the thread engages with the bore. This allows for very a precise fit of the implant. Preferably, the base member is cylindrically formed in the portion of the sliding seat.

It can be provided in yet another embodiment that the annular ridges and/or recesses are arranged at least at the end of the base member facing away from the thread. This is therefore the end which is inserted first into the bone. In the case of a dental implant this is therefore the lower end which is arranged in the jaw bone. Firm anchorage of the dental implant in the root zone is thereby enabled.

It can further also be provided that the annular recesses are adjacent to each other so that they form the ridges. Material forming the ridges therefore remains on the surface of the base member of the implant between the annular recesses. The annular recesses simultaneously form undercuts onto which bone material grows and thereby affixes the implant in the bone.

An advantageous embodiment can provide that the recesses are formed as annular groves and/or as concave indentations. The annular grooves result in a uniform anchorage of the base member in the jaw bone across the entire perimeter. The concave indentations, which, for example, can be formed like the surface of a golf ball also provide good uniform footing of the implant in the bone when the bone has grown to the implant. Preferably the recesses are evenly spaced.

It can be advantageously provided that the concave indentations are located on annular lines. In this case, the concave recesses being located on two adjacent annular lines respectively form annular ridges between themselves which guarantee good footing of the implant.

It can also be provided that the concave recesses on two annular lines located adjacent to each other are arranged offset to one another. Thereby, dense arrangement of concave recesses is achieved and good footing of the implant in the bones is enabled.

Yet another embodiment provides that the section of the base member on which the thread is arranged is shorter than the section of the base member on which no thread is arranged. This enables low pressure to the bone, while good footing of the implant in the bone is nevertheless achieved.

It can furthermore also be provided that the inner end of the base member is rounded. This is the end that is disposed into the bore in the bone. This enables good distribution of forces, the implant can be easily inserted into the bore, particularly when the base member is tapered to its inner end.

In a further embodiment it can be provided that the implant is made of ceramic, in particular zirconium oxide or aluminum oxide or a combination of these two oxide ceramics. As a result, a firm tooth-colored implant is provided.

It can be provided in yet another advantageous embodiment that the surface of the base member comprises microroughness. This micro-roughness improves bone growth onto the implant.

The invention is further illustrated in more detail using the figures.

Figure 1:
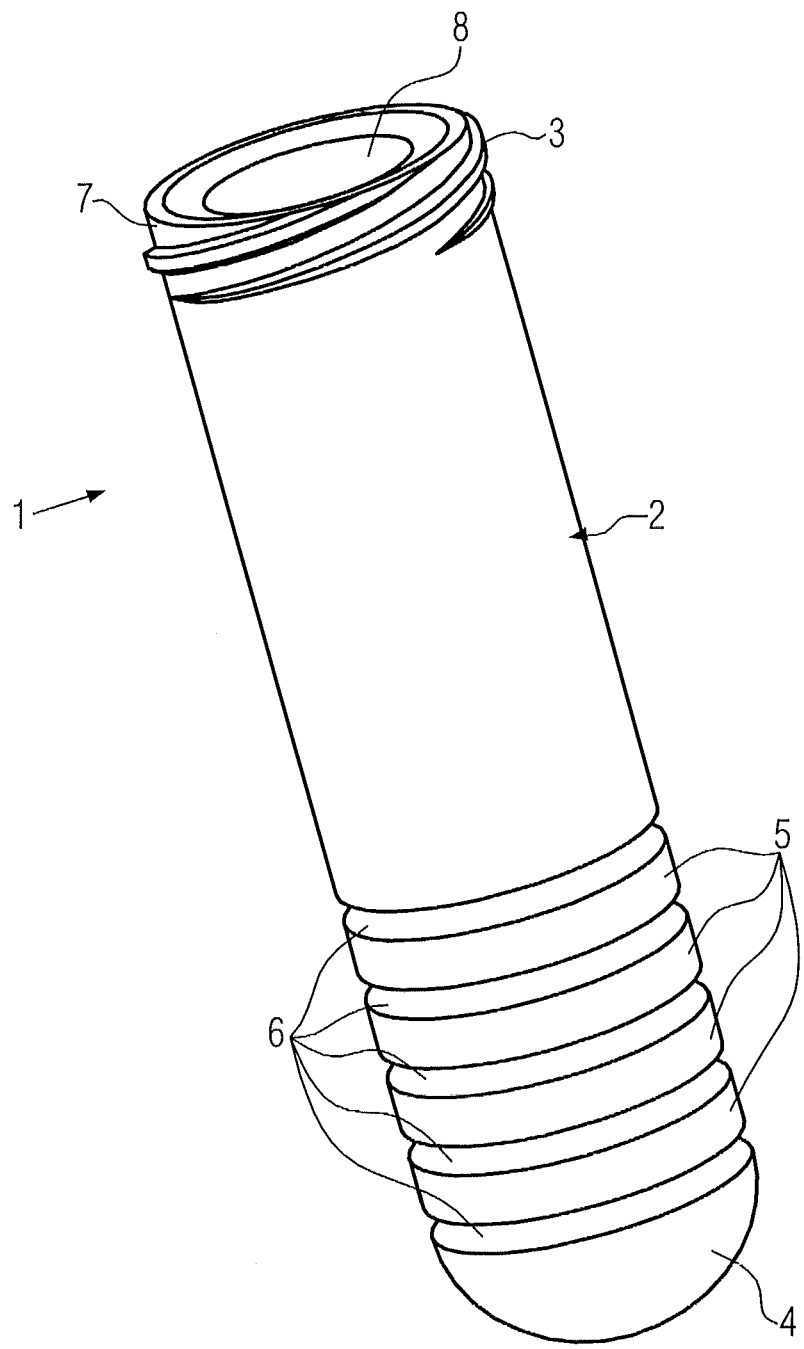
FIG. 1 shows a first embodiment of a dental implant.

FIG. 1 shows a first embodiment of the implant as a dental implant 1. However, an embodiment as an implantable screw or as an implantable connection element is conceivable. The dental implant 1 comprises a base member 2 which is formed substantially cylindrically. At its outer end, i.e., at the end which when the dental implant is inserted faces towards the oral cavity, a thread 3 is disposed on the base member 2. The opposite end of the base member 2 is rounded, i.e. the inner end which is disposed in the jaw bone when the base member 2 is inserted. In FIG. 1, the inner end 4 is hemispherical. Between the inner end 4 and the thread 3, annular ridges 5 and annular recesses 6 are formed on the surface of the base member 2. The recesses 6 have the shape of grooves extending circularly around the perimeter of the base member 2. The grooves 6 are arranged adjacent to each other so that material remaining on the surface of the base member 2 between the grooves 6 forms the ridges 5. The grooves 6 and therefore also the ridges 5 are arranged near the inner end 4 and extend across approximately one third to one half of the base member 2. The remaining portion of the base member 2 from the grooves 6 to the thread 3 has a smooth surface. In this manner, the entire base member 2 has no elements which project beyond the surface of the base member 2 except in the portion in which the thread 3 is arranged. Thereby the section of the base member 2 on which no thread is arranged is formed as a sliding seat. The dental implant 1 can then be easily inserted into a cylindrical bore in the jaw bone without any stress or pressure being exerted on the surrounding tissue.

The thread 3 is preferably designed as a tapping or groove thread. The thread 3, as described above, is arranged at the outer end 7 of the implant base member 2. The thread 3 extends over a maximum of one tenth of the total length of the base member 2. The thread 3 is designed with multiple entries, and therefore comprises two or more threads turns. This enables secure and precise footing of the dental implant 1 in the jaw even with the short length of the thread 3. Due to undercuts in the implant base member 2 formed by the grooves 6, growth of the jaw bone to the dental implant 1 is facilitated. It can also be provided that the surface of the implant 1 comprises microroughnesses which again lead to improved growth of the jaw bone onto the implant. Due to the short length of the thread 3, the dental implant can be locked in the jaw bone by a short turn, preferably a turn by one half or one quarter of the perimeter of the dental implant 1.

Preferably the implant is fabricated from ceramic, in particular from zirconium oxide. The implant can be formed in one piece or in two pieces. In the one-piece design, the attachment of the superstructure, i.e. a crown or a bridge, is performed directly onto the dental implant being inserted in the jaw bone. In a two-piece design, an abutment is fastened to the base member, the superstructure is fixed to the abutment. FIG. 1 is illustrated as a two-piece design. At the outer end 7 of the base member 2, a bore 8 is provided in which an abutment can be attached.

Figure 2:
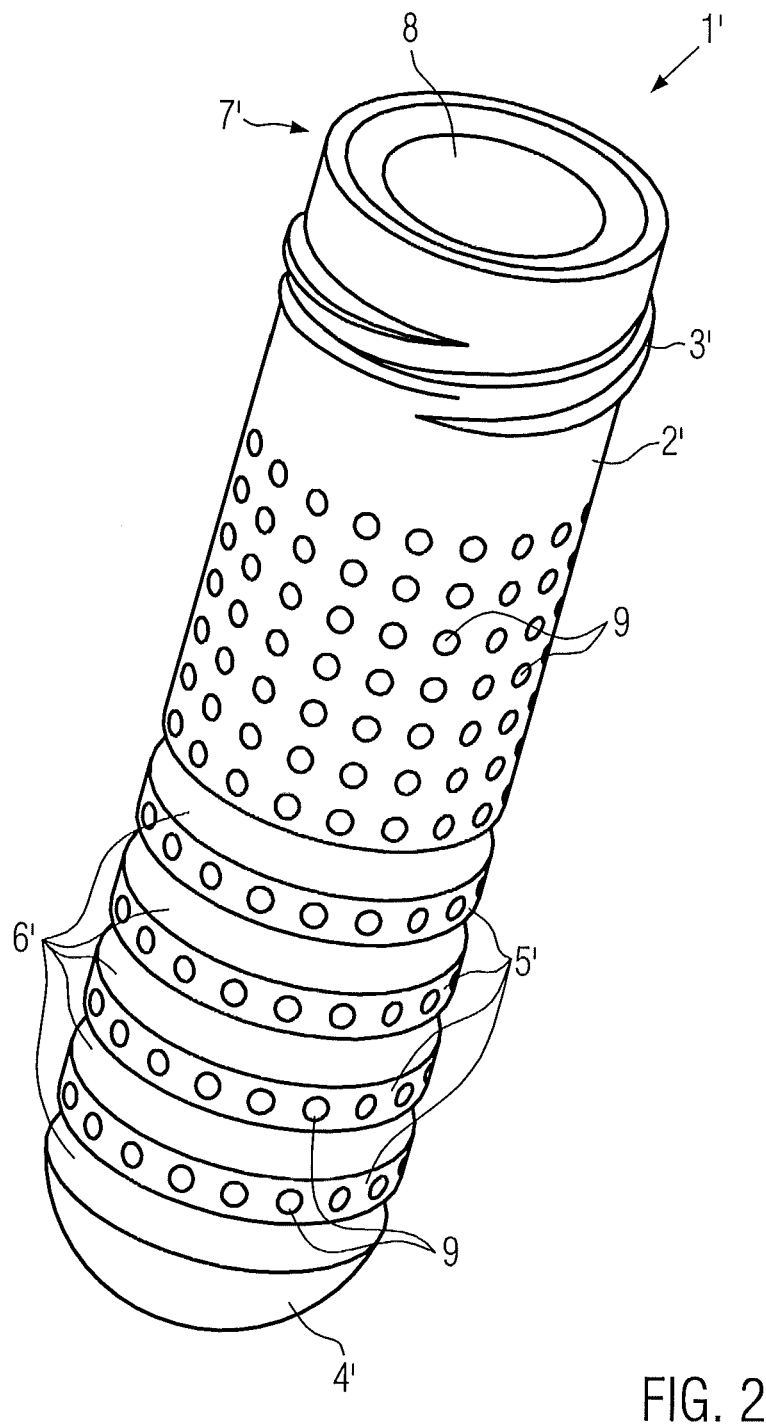
FIG. 2 shows a second embodiment of a dental implant.

FIG. 2 shows another embodiment of a dental implant 1' according to the invention. This dental implant is structured as being substantially identical to the dental implant of FIG. 1. The differences are indicated below. The dental implant 1' also comprises a base member 2'. The thread 3' is disposed at the outer end 7' of the base member 2'. This thread 3' as well is formed with multiple entries. The length of the section of the base member 2' on which the thread 3' is disposed here as well corresponds to a maximum one tenth of the total length of the implant base member 2'.

The inner end 4' of the base member 2' is again rounded, preferably hemispherically. Starting from the inner end 4' of the base member 2', recesses are formed in the surface of the base member 2'. These recesses have the shape of circular grooves 6' extending around the perimeter of the base member 2' and forming closed rings. It could also be possible that the grooves are interrupted and extend diagonally on the surface of the base member 2' as long as the pitch of a groove for a complete turn around the perimeter of the base member 2' equals to zero. This means that the grooves 6' are not spiral-shaped or helical and unscrewing of the implant after insertion into the jaw bone is thereby prevented. Here as well, the grooves 6' are disposed adjacent to each other so that ridges 5' remain on the surface of the base member 2' between two grooves 6'. The grooves 6' therefore form undercuts in the base member 2' into which the jaw bone can grow. In order to further facilitate growth of the jaw bone onto the implant 1', additional concave indentations 9' are formed on the surface of the base member 2'. These concave indentations 9 are arranged on both the ridges 5' as well as in the portion of the base member 2', in which neither grooves 6' nor any thread 3' is disposed. Preferably, these concave indentations 9 have the shape like the surface of a golf ball (dimple). Like the dental implant 1 shown in FIG. 1, the dental implant 1' can comprise micro-roughnesses on the surface to further facilitate growth of the jaw bone. In addition, the portion of the base member 2', on which no thread is arranged, is formed as a sliding seat. This means that this portion comprises no elements extending beyond the actual surface of the base member 2', so that the base member 2' can be easily inserted into a bore in the jaw bone without applying much pressure onto the bone. A bore 8 for receiving an abutment is again fitted at the outer end 7' of the dental implant 1. The concave indentations 9 of the dental implant 1' in FIG. 2 are substantially circular in shape.

Figure 3:
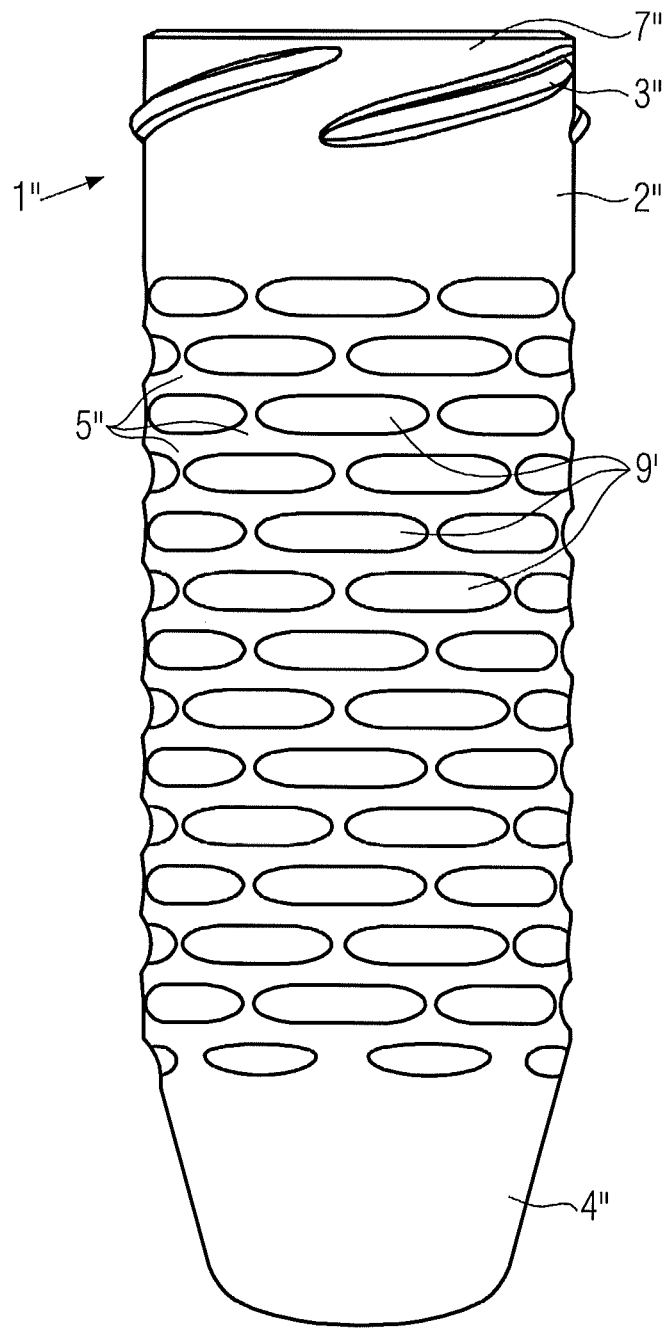
FIG. 3 shows a third embodiment of a dental implant.

FIG. 3 shows yet another embodiment of a dental implant 1". In the following, the differences to the previously described two dental implants are depicted below. The dental implant 1" again comprises a base member 2". A thread 3" is disposed at the outer end 4" of the base member 2". The thread 3" is formed with multiple entries and comprises four thread turns. Each of the thread turns extends across approximately one quarter of the perimeter of the dental implant 1". The thread 3" is again preferably a groove thread or a self-tapping thread. The implant 1" can then be easily inserted into a bore in the jawbone and be precisely affixed by a quarter turn. Concave indentations 9' are formed on the surface of the base member 2". The concave indentations 9' start just below the thread 3" and extend almost to the inner end 4" of the base member 2". The concave indentations 9' are approximately elliptical and at the transition to the surface of the base member 2" comprise rounded edges. This facilitates insertion of the implant 1" into a bore in the jawbone and the growth of the jaw bone. The concave indentations 9' are arranged on circular lines, where the circular lines extend around the perimeter of the base member 2" and each span a plane extending perpendicular to the longitudinal axis of the implant 1" and thereby also to the longitudinal axis of the base member 2". The concave indentations 9' on two adjacent circular lines are arranged offset from one another, so that a dense array of concave indentations 9' is obtained on the surface of the base member 2". The adjacent indentations 9' are spaced from each other, so that a circular ridge 5" running all around is formed between the grooves 9' on adjacent circular lines. These ridges 5", like in the two previous embodiments, result in the implant not being able to unscrew itself from the jaw bone, as may occur with screw implants.

The base member 2" of the dental implant 1''' is again formed substantially cylindrical. In the lower fifth of the dental implant, the diameter of the base member 2" decreases, so that the base member 2" tapers out conically downwards, i.e. towards the inner end 4". This facilitates insertion of the dental implant 1" into a bore in the jaw bone.

The dental implant 1" can in addition to the concave indentations 9' also have micro-roughnesses on the surface of the base member 2" in order to facilitate growth of the jaw bone.

The invention claimed is:

1. A dental implant anchorable in a jaw bone, the dental implant comprising:
    an inner end region configured to enter the jaw bone first when said dental implant is inserted into the jaw bone, and an outer end region configured to face towards an oral cavity of a mouth when the dental implant is implanted in said jaw bone, wherein said outer end region includes an outermost end of said dental implant and said inner end region includes an innermost end of said dental implant, and an entire length of said dental implant is defined as the length between the outermost end and the innermost end along a longitudinal axis of said dental implant;
    a bore hole;
    a threaded region arranged at said outer end region of said dental implant, and said threaded region is apically in direct contact with said outermost end of said dental implant or a cylindrical region arranged at said outer end region and in direct contact with said outermost end; and
    a non-threaded region arranged apical to said threaded region, said non-threaded region having annular ridges or annular recesses,
    wherein a length of said threaded region corresponds to approximately one tenth of said entire length of said dental implant, said threaded region having multiple individual thread spirals, each of said multiple individual thread spirals has an entry arranged at a same axial position that is normal to the longitudinal axis of said dental implant, and wherein a length of each of said multiple individual thread spirals is less than a perimeter of said dental implant.

2. The dental implant according to claim 1, wherein said annular ridges or said annular recesses are closed.

3. The dental implant according to claim 1, wherein a section of said dental implant is formed as a sliding seat.

4. The dental implant according to claim 1, wherein said annular ridges or said annular recesses are disposed on said inner end region of said dental implant.

5. The dental implant according to claim 1, wherein said annular recesses are located adjacent to one another such that they form ridges.

6. The dental implant according to claim 1, wherein said annular recesses are formed as annular grooves or concave indentations.

7. The dental implant according to claim 6, comprising said concave indentations located on annular lines.

8. The dental implant according to claim 7, wherein said concave indentations are arranged offset to one another on two adjacent annular lines.

9. The dental implant according to claim 1, wherein said inner end region of said dental implant is rounded.

10. The dental implant according to claim 1, made from ceramic, including zirconium oxide or aluminum oxide or a combination of both zirconium and aluminum oxide ceramics.

11. The dental implant according to claim 1, wherein a surface of said dental implant comprises: microroughnesses.

12. The dental implant according to claim 1, wherein said length of each of said multiple thread spirals is about one quarter of said perimeter of said dental implant.

13. The dental implant according to claim 2, wherein a section of said dental implant is formed as a sliding seat.

14. The dental implant according to claim 13, wherein said annular ridges or annular recesses are disposed on said inner end region of said dental implant.

15. The dental implant according to claim 14, wherein said inner end region of said dental implant is rounded.

16. The dental implant according to claim 15, made from ceramic, including zirconium oxide or aluminum oxide or a combination of both zirconium and aluminum oxide ceramics.

17. The dental implant according to claim 16, wherein a surface of said dental implant comprises: microroughnesses.

* * * * *